United States Patent [19]

Rehr et al.

[11] Patent Number: 5,190,869

[45] Date of Patent: Mar. 2, 1993

[54] PROCESS FOR OBTAINING SORBITOL AND GLUCONIC ACID OR GLUCONATE USING *ZYMOMONAS MOBILIS*

[75] Inventors: Bert Rehr, Kelkheim; Hermann Sahm, Juelich, both of Fed. Rep. of Germany

[73] Assignee: Forschungszentrum Juelich GmbH, Juelich, Fed. Rep. of Germany

[21] Appl. No.: 706,333

[22] Filed: May 28, 1991

[30] Foreign Application Priority Data

May 28, 1990 [DE] Fed. Rep. of Germany ....... 4017103

[51] Int. Cl.$^5$ .......................... C12P 7/58; C12P 7/18; C12N 11/04; C12N 1/38
[52] U.S. Cl. ..................................... 435/137; 435/135; 435/136; 435/146; 435/158; 435/176; 435/177; 435/178; 435/179; 435/182; 435/253.6; 435/822
[58] Field of Search ............... 435/135, 136, 137, 146, 435/158, 822, 176, 178, 179, 182, 177, 253.6

[56] References Cited

U.S. PATENT DOCUMENTS

| | | | |
|---|---|---|---|
| 4,347,320 | 8/1982 | Borglum | 435/161 |
| 4,477,569 | 10/1984 | Schneider et al. | 435/161 |
| 4,526,867 | 7/1985 | Chibata et al. | 435/179 |
| 4,605,622 | 8/1986 | Hasegawa et al. | 435/179 |
| 4,755,467 | 7/1988 | Scopes et al. | 435/125 |
| 4,800,160 | 1/1989 | Iguchi et al. | 435/182 |
| 4,996,150 | 2/1991 | Joung et al. | 435/179 |
| 5,017,485 | 5/1991 | Bringer-Meyer | 435/158 |
| 5,037,740 | 8/1991 | Tanaka et al. | 435/182 |
| 5,102,795 | 4/1992 | Rehr et al. | 435/137 |

FOREIGN PATENT DOCUMENTS 3936757 11/1989 Fed. Rep. of Germany .

OTHER PUBLICATIONS

Chun et al., "The Simultaneous Production of Sorbitol From Fructose and Cluconic Acid From Glucose Using An Oxidoreductase of *Zymomonas mobilis*", Applied Microbiology Biotechnology, vol. 29, pp. 19–24, 1988.

Paterson et al., "Sorbitol and Gluconate Production In A Hollow Fibre Membrane Reactor by Immobilized *Zymomonas mobilis*", Biocatalysis, vol. 1, pp. 217–229, 1988.

Bomar, "A Simple Procedure To Immobilize Microbial Cells", pp. 424–426.

Primary Examiner—Herbert J. Lilling
Attorney, Agent, or Firm—Foley & Lardner

[57] ABSTRACT

The long-term activity of the biocatalyst for the production of sorbitol and gluconic acid from an aqueous solution of fructose and glucose is considerably improved with the aid of permeabilized cells of *Zymomonas mobilis* immobilized using κ-carrageenan that has been rigidified and then stabilized by $K^+$ ions. Rigidification of κ-carrageenan is preferably carried out by treatment with glutaraldehyde alone or by treatment with polyethyleneimine or hexamethylenediamine and subsequent exposure to glutaraldehyde. A buffer-free solution is preferred and the pH is maintained by adding $Ca^{++}$ ions while simultaneously precipitating gluconic acid.

18 Claims, 1 Drawing Sheet

PROCESS FOR OBTAINING SORBITOL AND GLUCONIC ACID OR GLUCONATE USING ZYMOMONAS MOBILIS

BACKGROUND OF THE INVENTION

The present invention relates to a process for producing sorbitol and gluconic acid or gluconate from aqueous mixtures of fructose and glucose using permeabilized cells of Zymomonas mobilis in gel-immobilized form.

The production of sorbitol and gluconic acid starting from mixtures of glucose and fructose by means of Zymomonas mobilis is known. U.S. Pat. No. 4,755,467 describes the use of permeabilized cells for this process, and these methods are intended, where appropriate, to be employed in immobilized culture. Permeabilization of the cells was carried out by exposure to toluene, however, no disclosure of specific agents for the immobilization of such cells was disclosed.

A particularly expedient method of permeabilizing Zymomonas mobilis cells for the production of sorbitol and gluconic acid is described in German Patent Document 38 41 702 (=U.S. Ser. No. 448,334) now U.S. Pat. No. 5,017,485, in which a freezing technique is described. This method produces particularly useful permeabilized cells. In addition, a process for producing sorbitol and gluconic acid using Zymomonas mobilis cells permeabilized with a cationic surfactant is described in German Patent Application 39 36 757.6, which corresponds to U.S. Ser. No. 606,821 now U.S. Pat. No. 5,102,795 this application, the use of immobilized cells is also recommended, but no specific support materials are disclosed.

The use of inorganic support materials such as, in particular, sintered glass or ceramic is widespread in biotechnological processes. M. T. Bomer proposes, in ZFL 6/85, pages 424–425, the use of agar gel or alginates as support materials for the immobilization of microorganisms, such as E. coli. In such applications, agar gel is preferred because of its low toxicity.

D. H. Chun et al. (Appl. Microbiol. Biotechnol. 29: 19-24 (1988)) describe the production of sorbitol and gluconic acid using toluene-permeabilized cells of Zymomonas mobilis immobilized in sodium alginate/Celite ® mixtures. These immobilizates are rigidified with a calcium chloride solution.

S. L. Paterson (Biocatalysis vol. 1, pages 217–229 (1989)) describes the production of sorbitol and gluconic acid in a hollow-fiber membrane reactor in which toluene-treated cells of Zymomonas mobilis are "immobilized."

In the processes described above, the efficiency of production of sorbitol and gluconic acid is improved by the use of permeabilized cells because no nutrients are needed for biomass production. There is, however, a relatively rapid decrease in the activity of the enzymes important to the conversion process. Thus, for example, in some of the processes described, a decrease in the conversion rate of more than 5% after 5 days or of about 1.5-1.8% after 10.5 days, respectively, was reported.

SUMMARY OF THE INVENTION

It is therefore an object of the present invention to provide a process for preparing sorbitol and gluconic acid using immobilized permeabilized cells of Zymomonas mobilis, in which the long-term activity of the biocatalyst is improved.

These and other objects according to the invention are provided by a process for obtaining sorbitol, gluconic acid and gluconate starting from an aqueous solution of fructose and glucose, comprising the steps of:

(a) permeabilizing cells of Zymomonas mobilis;

(b) immobilizing the permeabilized cells in a gel with κ-carrageenan;

(c) stabilizing the cells with $K^+$ ions;

(d) rigidifying the stabilized cells with either an aldehyde or a combination of an amine and an aldehyde; and (e) converting fructose and glucose in an aqueous solution into sorbitol, gluconic acid and gluconate with the stabilized, immobilized cells.

The invention also provides cells of Zymomonas mobilis that are immobilized in a gel with κ-carrageenan, stabilized with $K^+$ ions and rigidified with either an aldehyde or a combination of an amine and an aldehyde.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION OF THE PREFERRED EMBODIMENTS

Figure 1:
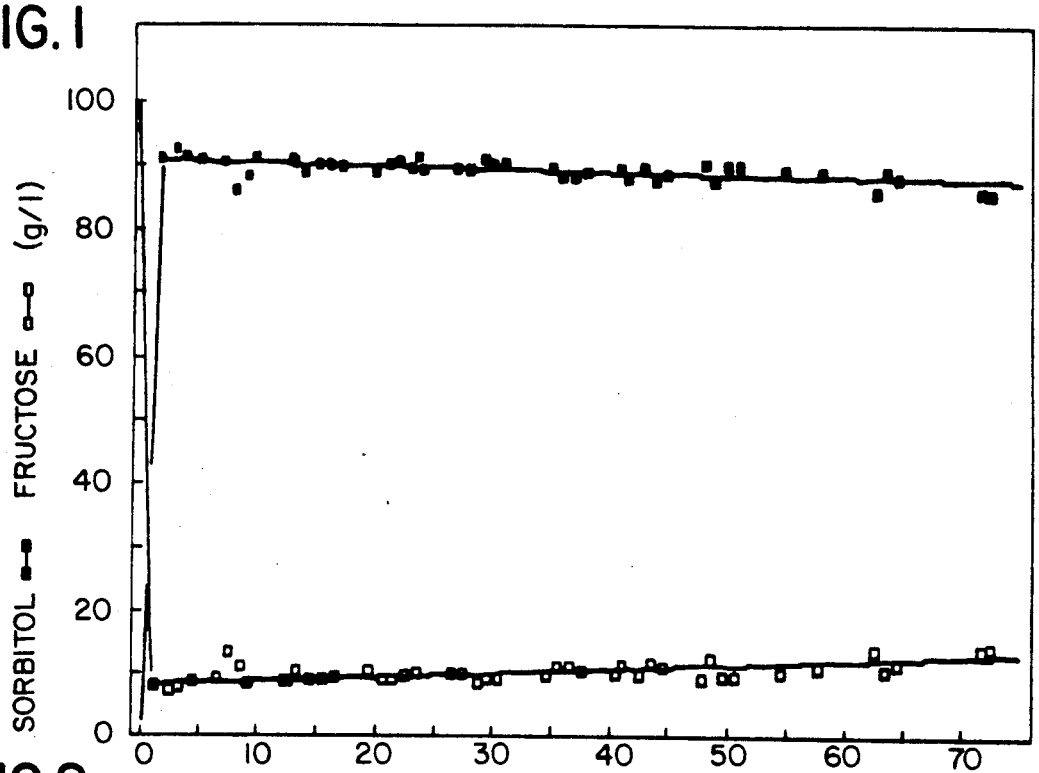
FIGS. 1 and 2 are plots of the continuous production of sorbitol and gluconic acid. They relate to the production of sorbitol and gluconic acid with the aid of cetyl trimethyl ammonium bromide (CTAB)-treated cells of Zymomonas mobilis which were immobilized on rigid κ-carrageenan beads. The substrate solution contained 100 g/l glucose and 100 g/l fructose. The dilution rate (D) was 0.055 $h^{-1}$. The protein concentration was 8.6 g/l.

The process according to the present invention comprises the use of κ-carrageenan immobilizates that are rigidified and then stabilized by $K^+$ ions. The κ-carrageenan immobilizate is preferably rigidified or hardened by treatment with glutaraldehyde or by successive treatment with polyethyleneimine or hexamethylenediamine and subsequent exposure to glutaraldehyde.

In a particularly preferred embodiment, Zymomonas mobilis cells are permeabilized by treatment with a cationic surfactant as described in German Patent Application P 39 36 757.6-41. In another preferred embodiment, cells are immobilized using a 2-8% carrageenan solution. In a particularly preferred embodiment, a 4% carrageenan solution is used for immobilization.

The κ-carrageenan immobilizates are stabilized using $K^+$ ions. In a preferred embodiment, stabilization is carried out by exposing such immobilizates to a KCl solution at temperatures not exceeding room temperature for a period of time ranging from several hours to days. In a particularly preferred embodiment, the immobilizates are exposed to a 0.1–1M KCl solution at refrigerator temperatures (approximately 4–8° C).

While buffered systems are normally used, it is particularly expedient according to the present invention to insure that the pH is kept constant by pH titration. For this purpose, KOH is particularly suitable because there is no disadvantageous depletion of K+ in the reaction medium when the fermentation process is carried out continuously. In a preferred embodiment, pH titration is carried out with simultaneous precipitation of gluconic acid by the addition of Ca++ solution.

Carrageenan immobilizate particles, especially in the form of cubes or beads, stabilized as described above, are then rigidified by treatment, preferably at pH 7 (HCl-neutralized), with aqueous polyethyleneimine solution at a concentration of, for example, about 1%. The particles are then treated with a glutaraldehyde solution at a concentration of, for example, about 0.5%. While the concentration of polyethyleneimine and glutaraldehyde are not critical, in a preferred embodiment the concentration of these solutions is between about 0.3 and 3%. In a preferred embodiment, the particles are treated with polyethyleneimine and glutaraldehye at approximately 4-8° C. (refrigerated), however, in no case should the temperature exceed room temperature during such treatment. Rigidification or hardening can require approximately 0.5-2 hours. Exposure times of about 0.5 hour in each step are preferred. In an alternative method of rigidification, glutaraldehyde alone or a solution of hexamethylenediamine (at first) and then a solution of glutaraldehyde (at second) can be employed. Of course, rigidification can also be carried out with other aldehydes or amines/aldehydes.

The production of sorbitol and gluconic acid using carrageenan immobilizates of permeabilized *Zymomonas mobilis* cells is known (see, for example, German Patent Application P 39 36 757.6-41). This process is preferably carried out at about 38° C. and about pH 6.4.

The invention is explained in more detail in the following illustrative examples.

EXAMPLE 1

Effect of Various Rigidification Methods on the Activity of the Immobilizate

Twenty ml of a suspension of CTAB-permeabilized cells of *Zymomonas mobilis* were mixed with 80 ml of a 4% carrageenan solution and the mixture was poured into shallow dishes and allowed to rigidify. The rigidified immobilizate was then divided into 3×3×3 mm cubes, exposed to a solution of 0.3M KCl overnight and then divided into batches and exposed to one of the following treatments:

(A) Cubes stabilized with potassium ions were used without further treatment for production of sorbitol/gluconic acid.

(B) Cubes were incubated in aqueous glutaraldehyde solution at 4° C. for 30 minutes as presented in Table 1.

(C) Cubes subjected to the treatment described in paragraph (A) above were incubated with a 0.1% solution of hexamethylenediamine (HMDA) at 4° C. for 30 minutes and then treated with glutaraldehyde as described in paragraph (B).

(D) Cubes subjected to the treatment described in paragraph (A) above were incubated with a 1.0% solution of polyethyleneimine at room temperature for 30 minutes and then treated with glutaraldehyde as described in paragraph (B).

After such treatments, all of the cubes were washed with potassium citrate buffer and then the activity of each batch was assayed using a solution comprised of 10% glucose/10% fructose. The results are presented in the following tables.

TABLE 1

Treatment with glutaraldehyde

|  | without glutaraldehyde | glutaraldehyde concentration | | |
|---|---|---|---|---|
|  |  | 0.2% | 0.5% | 0.85% |
| g sorbitol/l × h | 10.7 | 11.6 | 10.7 | 11.5 |
| g sorbitol/g protein × h | 2.7 | 2.65 | 2.7 | 2.6 |

TABLE 2

TREATMENT WITH HEXAMETHYLENEDIAMINE (0.1%) AND GLUTARALDEHYDE

|  | without glutaraldehyde | glutaraldehyde concentration (all samples with HMDA) | | |
|---|---|---|---|---|
|  |  | 0.2% | 0.5% | 0.85% |
| g sorbitol/l × h | 10.7 | 8.5 | 9.0 | 9.1 |
| g sorbitol/g protein × h | 2.7 | 2.16 | 2.27 | 2.3 |

TABLE 3

TREATMENT WITH POLYETHYLENEIMINE (1.0%) AND GLUTARALDEHYDE

|  | without glutaraldehyde | glutaraldehyde concentration (all samples with PEI) | | |
|---|---|---|---|---|
|  |  | 0.2% | 0.5% | 0.85% |
| g sorbitol/l × h | 10.0 | 9.4 | 9.4 | 9.2 |
| g sorbitol/g protein × h | 2.7 | 2.37 | 2.37 | 2.32 |

EXAMPLE 2

Comparison of Two Rigidification Methods

A volume of 450 ml of cubes treated by the method described in Example 1 (A) were reacted in a 1.5 liter fluidized bed fermenter with a substrate solution comprised of 100 g/l glucose, 100 g/l fructose and a protein concentration of 6.1 g/l, at a D of 0.053 h$^{-1}$, and titrated with 3N KOH. After 48 hours, 68.8% of the substrate was converted with a resulting production of 3.65 g sorbitol/l×h and 0.6 g sorbitol/g protein×h. After approximately fifty (50) days, the productivity of the fermenter was reduced by about one half. Cubes treated as described in Example 1 (D) using glutaraldehyde at a concentration of 0.5%, were reacted in a 1.6 liter fermenter with a substrate solution comprised of 100 g/l glucose, 100 g/l fructose and a protein concentration of 8.6 g/l, at a D of 0.055 h$^{-1}$, and titrated with 3 N KOH. After 48 hours, 90.0% of the substrate was converted with a resulting production of 4.95 g sorbitol/l×h and 0 58 g sorbitol/g protein×h. After seventy-five (75) days, the productivity of the fermenter was reduced by only 3.5%.

Figure 2:
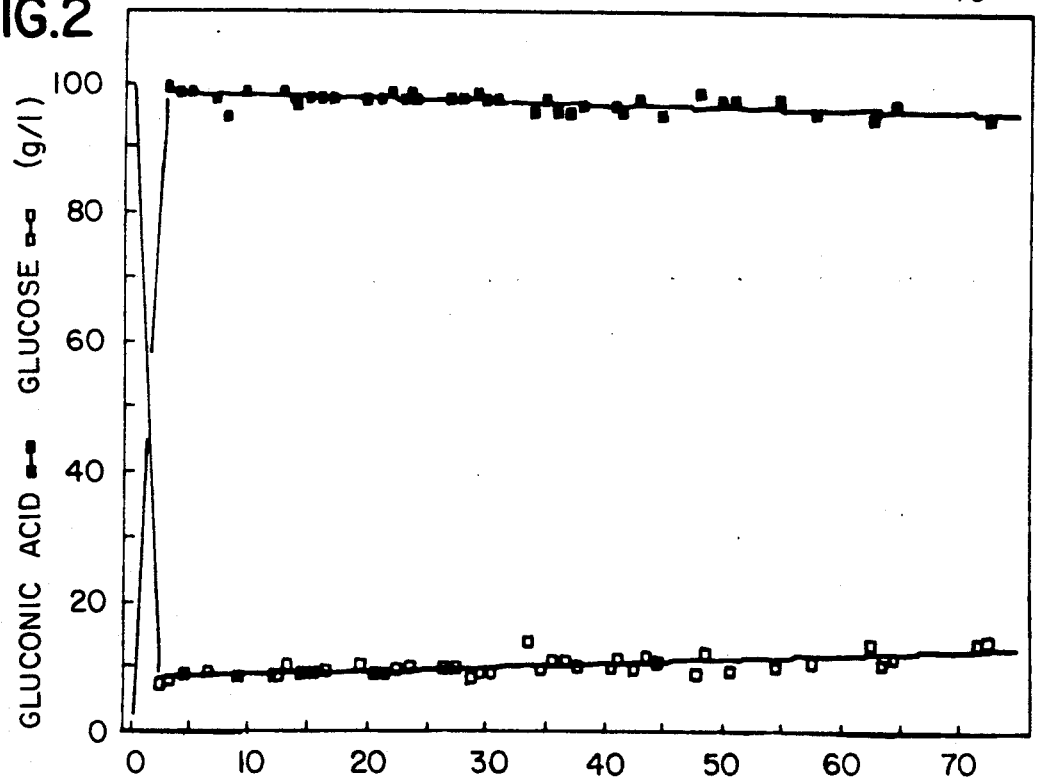

FIGS. 1 and 2 show the production of sorbitol and gluconic acid, respectively, in this long-term experiment.

The yield of sorbitol and gluconic acid can be increased to 98% by decreasing D. D can be decreased, for example, by using two reactors in series.

What is claimed is:

1. A process for obtaining at least one of sorbitol, gluconic acid and gluconate starting from an aqueous solution of at least one of fructose and glucose, comprising the steps of:
   permeabilizing cells of *Zymomonas mobilis*;
   immobilizing the permeabilized cells in a gel with κ-carrageenan;
   stabilizing the cells with K+ ions;

rigidifying the stabilized cells with either an aldehyde or a combination of an amine and an aldehyde, said aldehyde or amine/aldehyde combination being selected from the group consisting of glutaraldehyde, a combination of glutaraldehyde and hexamethylenediamine and a combination of glutaraldehyde and polyethyleneimine; and converting an aqueous solution of at least one of fructose and glucose into at least one of sorbitol, gluconic acid and gluconate with the stabilized, immobilized cells.

2. The process as claimed in claim 1, wherein the rigidifying step comprises treatment with glutaraldehyde.

3. The process as claimed in claim 1, wherein the rigidifying step comprises treatment with hexamethylenediamine and glutaraldehyde.

4. The process as claimed in claim 1, wherein the rigidifying step comprises treatment with polyethyleneimine and glutaraldehyde.

5. The process as claimed in claim 1, wherein the step of converting is carried out in buffer-free solution and wherein the pH is kept constant by pH titration.

6. The process as claimed in claim 5, wherein the titration is carried out with KOH.

7. The process as claimed in claim 5, wherein the converting step comprises conversion of an aqueous solution of glucose into gluconic acid and wherein pH titration is carried out simultaneously with a precipitation of the gluconic acid by addition of $Ca^{++}$ ions.

8. The process as claimed in claim 1, wherein the rigidifying step comprises successive treatment with hexamethylenediamine and glutaraldehyde.

9. The process as claimed in claim 1, wherein the rigidifying step comprises successive treatment with polyethyleneimine and glutaraldehyde.

10. The process as claimed in claim 1, wherein the permeabilizing step comprises treatment of cells of *Zymomonas mobilis* with a cationic surfactant.

11. The process as claimed in claim 1, wherein the immobilizing steps comprises treatment with about 2–8% carrageenan.

12. The process as claimed in claim 1, wherein the stabilizing step comprises treatment with KCl solution.

13. The process as claimed in claim 12, wherein the immobilized cells are refrigerated during the stabilizing step.

14. The process as claimed in claim 1, wherein the converting step is carried out in two reactors connected in series.

15. The process as claimed in claim 1, wherein the converting step comprises conversion of an aqueous mixture of glucose and fructose.

16. Cells of *Zymomonas mobilis* that are permeabilized, immobilized in a gel with κ-carrageenan, stabilized with $K^+$ ions and rigidified with either an aldehyde or a combination of an amine and an aldehyde, said aldehyde or amine/aldehyde combination being selected from the group consisting of glutaraldehyde, a combination of glutaraldehyde and hexamethylenediamine and a combination of glutaraldehyde and polyethyleneimine.

17. The cells as claimed in claim 16, wherein the cells are permeabilized by treatment with a cationic surfactant.

18. The cells as claimed in claim 17, wherein the cationic surfactant is cetyl trimethyl ammonium bromide.

* * * * *